US012044678B2

(12) United States Patent
Sundvor et al.

(10) Patent No.: US 12,044,678 B2
(45) Date of Patent: Jul. 23, 2024

(54) PORTABLE DEVICE FOR DETECTION OF HARMFUL SUBSTANCES (71) Applicant: Nima Acquisition, LLC, Northfield, IL (US)

(72) Inventors: Scott Sundvor, San Francisco, CA (US); John Paul Walton, San Francisco, CA (US); Jonathan William Kiel, San Francisco, CA (US); Jeffrey Mekler, San Francisco, MA (US); Shireen Taleghani, San Francisco, CA (US); Jacob Mooney, San Francisco, CA (US)

(73) Assignee: Nima Acquisition, LLC, Northfield, IL (US)

( * ) Notice: Subject to any disclaimer, the term of this patent is extended or adjusted under 35 U.S.C. 154(b) by 464 days.

(21) Appl. No.: 16/791,116

(22) Filed: Feb. 14, 2020

(65) Prior Publication Data

US 2020/0200738 A1 Jun. 25, 2020

Related U.S. Application Data (60) Division of application No. 15/910,692, filed on Mar. 2, 2018, now abandoned, which is a continuation of
(Continued)

(51) Int. Cl.
*G01N 33/52* (2006.01)
*G01N 1/28* (2006.01)
(Continued)

(52) U.S. Cl.
CPC .......... *G01N 33/521* (2013.01); *G01N 33/02* (2013.01); *G01N 33/5308* (2013.01); *G01N 2001/2866* (2013.01)

(58) Field of Classification Search
CPC ...... G01N 22/521; G01N 33/02; G01N 33/52; G01N 33/5308; G01N 2001/2866
See application file for complete search history.

(56) References Cited

U.S. PATENT DOCUMENTS 3,802,842 A 4/1974 Lange et al.
4,066,511 A 1/1978 Montagnon
(Continued)

FOREIGN PATENT DOCUMENTS

CN 101166569 A 4/2008
CN 101909757 A 12/2010
(Continued)

OTHER PUBLICATIONS

Anonymous: "Food Allergen Handbook", Internet Citation, Jan. 1, 2012 (Jan. 1, 2012), pp. 1-28, XP008183485, http://web.archive.org/web/20160122220553.
(Continued)

*Primary Examiner* — Brian J. Sines
(74) *Attorney, Agent, or Firm* — Quarles & Brady LLP (57) ABSTRACT A self-contained apparatus and methods for detecting the presence of any specified substance in any medium. A sample of the medium is placed in a capsule, along with a solvent and a sensor configured to test for a target analyte. The solvent comes into contact with the medium in the capsule, and the capsule is agitated to create a dispersion in the solvent of a portion of any target analyte present in the medium. A release mechanism configured to cause conduction of the dispersion to the sensor, so that the sensor produces an indication of presence of the target analyte if the target analyte is present in the medium. The apparatus uses a disposable capsule where the medium in question is placed and the disposable capsule is placed inside a reader and analyzed for presence of the harmful substance.

19 Claims, 6 Drawing Sheets

Related U.S. Application Data application No. 14/227,543, filed on Mar. 27, 2014, now Pat. No. 9,939,431, application No. 16/791,116 is a division of application No. 14/227,543, filed on Mar. 27, 2014, now Pat. No. 9,939,431.

(60) Provisional application No. 61/874,590, filed on Sep. 6, 2013, provisional application No. 61/806,425, filed on Mar. 29, 2013.

(51) Int. Cl.
*G01N 33/02* (2006.01)
*G01N 33/53* (2006.01)

(56) References Cited

U.S. PATENT DOCUMENTS

| | | |
|---|---|---|
| 4,250,256 A | 2/1981 | Bleisteiner et al. |
| 4,822,174 A | 4/1989 | Deibel |
| 4,960,691 A | 10/1990 | Gordon et al. |
| 5,143,084 A | 9/1992 | Macemon et al. |
| 5,217,905 A | 6/1993 | Marchand et al. |
| 5,256,372 A | 10/1993 | Brooks et al. |
| 5,415,994 A | 5/1995 | Imrich et al. |
| 5,504,013 A | 4/1996 | Senior |
| 6,136,549 A | 10/2000 | Feistel |
| 6,136,610 A | 10/2000 | Polito et al. |
| 6,180,335 B1 | 1/2001 | Wilkins et al. |
| 6,319,466 B1 | 11/2001 | Markovsky et al. |
| 6,528,323 B1 | 3/2003 | Thayer et al. |
| 6,616,893 B1 | 9/2003 | Pham |
| 6,663,833 B1 | 12/2003 | Stave et al. |
| 6,881,554 B2 | 4/2005 | Dicesare et al. |
| 7,098,040 B2 | 8/2006 | Kaylor et al. |
| 7,220,597 B2 | 5/2007 | Zin et al. |
| 7,238,322 B2 | 7/2007 | Wang et al. |
| 7,267,799 B1 | 9/2007 | Borich et al. |
| 7,300,197 B2 | 11/2007 | McCurdy et al. |
| 7,371,582 B2 | 5/2008 | Nahm et al. |
| 7,507,374 B2 | 3/2009 | Gould et al. |
| 7,527,765 B2 | 5/2009 | Royds |
| 7,560,272 B2 | 7/2009 | Ramsey et al. |
| 7,585,529 B2 | 9/2009 | Villar et al. |
| 7,749,771 B2 | 7/2010 | Burgess-Cassler et al. |
| 7,776,266 B2 | 8/2010 | Royds |
| 7,784,678 B2 | 8/2010 | Kuo et al. |
| 7,932,099 B2 | 4/2011 | Egan et al. |
| 7,972,871 B2 | 7/2011 | Chandler |
| 7,995,196 B1 | 8/2011 | Fraser |
| 8,211,715 B1 | 7/2012 | Royds |
| 8,231,548 B2 | 7/2012 | Hoenes |
| 8,278,091 B2 | 10/2012 | Rutter et al. |
| 8,361,460 B2 | 1/2013 | Morimatsu et al. |
| 8,632,730 B2 | 1/2014 | Petrilla et al. |
| 9,005,551 B2 | 4/2015 | Chen et al. |
| 9,201,068 B2 | 12/2015 | Suni et al. |
| 9,285,331 B2 * | 3/2016 | Minteer ............... G01N 35/026 |
| 9,625,357 B2 | 4/2017 | Bransky et al. |
| 10,533,995 B2 | 1/2020 | Sundvor |
| 2003/0138819 A1 | 7/2003 | Gong et al. |
| 2003/0138941 A1 | 7/2003 | Gong et al. |
| 2003/0186458 A1 | 10/2003 | Dicesare et al. |
| 2004/0018575 A1 | 1/2004 | Rappin et al. |
| 2004/0022687 A1 | 2/2004 | Wuske et al. |
| 2004/0132091 A1 | 7/2004 | Ramsey et al. |
| 2004/0137137 A1 | 7/2004 | Villar et al. |
| 2004/0141879 A1 | 7/2004 | Loomis |
| 2004/0152209 A1 | 8/2004 | Zin et al. |
| 2004/0189311 A1 | 9/2004 | Glezer et al. |
| 2004/0265234 A1 | 12/2004 | Morimatsu et al. |
| 2005/0112779 A1 | 5/2005 | Wei et al. |
| 2005/0136553 A1 | 6/2005 | Kaylor et al. |
| 2005/0147532 A1 | 7/2005 | Bellet |
| 2005/0214866 A1 | 9/2005 | McCall et al. |
| 2005/0214951 A1 | 9/2005 | Nahm et al. |
| 2005/0255533 A1 | 11/2005 | Dantini et al. |
| 2006/0051237 A1 | 3/2006 | Wang et al. |
| 2006/0204399 A1 | 9/2006 | Freeman et al. |
| 2006/0240568 A1 | 10/2006 | Petruno |
| 2006/0292035 A1 | 12/2006 | Gould et al. |
| 2007/0041624 A1 | 2/2007 | Cork |
| 2007/0047382 A1 | 3/2007 | McCurdy et al. |
| 2007/0054414 A1 | 3/2007 | Burgess-Cassler et al. |
| 2007/0116595 A1 | 5/2007 | Petrilla et al. |
| 2007/0238102 A1 | 10/2007 | Song |
| 2007/0238138 A1 | 10/2007 | Royds |
| 2007/0292899 A1 | 12/2007 | Lovell et al. |
| 2007/0292941 A1 | 12/2007 | Handique et al. |
| 2008/0171397 A1 | 7/2008 | Hardcastle et al. |
| 2008/0181821 A1 | 7/2008 | Jung et al. |
| 2008/0199851 A1 | 8/2008 | Egan et al. |
| 2009/0047691 A1 | 2/2009 | Huwig et al. |
| 2009/0136633 A1 | 5/2009 | Royds |
| 2009/0148933 A1 | 6/2009 | Battrell et al. |
| 2009/0154776 A1 | 6/2009 | Mott |
| 2010/0129922 A1 | 5/2010 | Gold et al. |
| 2010/0167309 A1 | 7/2010 | Chandler |
| 2010/0210033 A1 | 8/2010 | Scott |
| 2010/0222224 A1 | 9/2010 | Suni et al. |
| 2010/0255609 A1 | 10/2010 | Rutter et al. |
| 2010/0317033 A1 | 12/2010 | Abdel |
| 2011/0039198 A1 | 2/2011 | Ashley et al. |
| 2011/0044865 A1 | 2/2011 | Groisman |
| 2011/0059550 A1 | 3/2011 | Haik |
| 2011/0143968 A1 | 6/2011 | Chen et al. |
| 2012/0046203 A1 | 2/2012 | Walsh |
| 2012/0078455 A1 | 3/2012 | Chrostowski et al. |
| 2012/0264232 A1 | 10/2012 | Kramer et al. |
| 2013/0203043 A1 | 8/2013 | Ozcan et al. |
| 2014/0033809 A1 * | 2/2014 | Bransky ............... G01N 1/2035 73/64.56 |
| 2014/0072960 A1 * | 3/2014 | Lansing ............. G01N 33/5302 435/7.1 |
| 2014/0120563 A1 | 5/2014 | Ozcan et al. |
| 2014/0125835 A1 | 5/2014 | Voss et al. |
| 2014/0174953 A1 | 6/2014 | Elder et al. |
| 2014/0186880 A1 | 7/2014 | Lowenkamp |
| 2014/0227796 A1 | 8/2014 | Gold et al. |
| 2014/0295406 A1 | 10/2014 | Sundvor et al. |
| 2014/0300696 A1 | 10/2014 | Ozcan et al. |
| 2015/0011020 A1 | 1/2015 | Sundvor et al. |
| 2015/0072358 A1 | 3/2015 | Luckert |
| 2015/0151300 A1 | 6/2015 | Williams et al. |
| 2017/0003222 A1 | 1/2017 | Neijzen et al. |
| 2019/0086430 A1 | 3/2019 | Wang |

FOREIGN PATENT DOCUMENTS

| | | | |
|---|---|---|---|
| CN | 102629689 B | 5/2014 | |
| CN | 102016574 B | 9/2014 | |
| EP | 1034429 B1 | 11/2003 | |
| EP | 1640718 A1 | 3/2006 | |
| WO | 1999014595 A1 | 3/1999 | |
| WO | WO-2005031351 A1 * | 4/2005 | ........... G01N 33/521 |
| WO | 2006117129 A1 | 11/2006 | |
| WO | 2011039198 A2 | 4/2011 | |
| WO | 2012078455 A1 | 6/2012 | |
| WO | 2014047692 A1 | 4/2014 | |
| WO | 2014176556 A1 | 10/2014 | |
| WO | 2015017442 A2 | 2/2015 | |

OTHER PUBLICATIONS

Extended European Search Report for EP Application No. 16762414.7 dated Oct. 11, 2018.
Office Action for Chinese Patent Application No. 201680014283.2 dated Apr. 3, 2019.
Wen et al., A novel extraction method for peanut allergenic proteins in chocolate and their detection by liposome-basec lateral flow assay, Eur. Food Res. Technol., 22(1), (2005), p. 564-569. (Year: 2005).
Woodfolk, et al., "Allergens, sources, particles and molecules: Why do we make IgE response,", Woodfolk et al., Allergens, sources, (56) References Cited

OTHER PUBLICATIONS particles and molecules: Why do we make IgE response, Allergol. Int. 2015, 64(4), (25 pages) (Year: 2015).

\* cited by examiner

PORTABLE DEVICE FOR DETECTION OF HARMFUL SUBSTANCES

CROSS-REFERENCE TO RELATED APPLICATIONS

This application is a divisional of U.S. application Ser. No. 15/910,692, filed 2 Mar. 2018, which is a continuation of U.S. patent application Ser. No. 14/227,543, filed 27 Mar. 2014, which claims the priority of U.S. Provisional Application Ser. No. 61/806,425, filed Mar. 29, 2013, and of U.S. Provisional Application Ser. No. 61/874,590, filed Sep. 6, 2013, all of which are incorporated herein by reference.

This application is a divisional of U.S. patent application Ser. No. 14/227,543 filed 27 Mar. 2014, issued as U.S. Pat. No. 9,939,431 of which is incorporated in its entirety by this reference.

TECHNICAL FIELD

The present invention is directed towards a consumer assay device and, more particularly, to a device suited for immediate, portable, point-of-use testing for specified substances within foods, medicines, cosmetics, etc.

BACKGROUND ART

Food, drinks, cosmetics, etc. are known to contain contaminants, toxins, allergens and other substances that may be harmful to some, or to all, consumers. Consumers who have a negative reaction to particular types of substances often have an extremely difficult time when dealing with products, such as restaurant food, a new type of lotion, new medicines, etc., because of the likelihood that these products might contain some substance that is harmful to them. For example, millions of children have a variety of food-related allergies to foods such as milk, eggs, soy, wheat, or other grains, or to particular proteins or other allergens, and it can be extremely difficult for them and their families to find suitable foods, especially while eating outside of the home. A device that could readily provide rapid diagnostics for harmful substances would be extremely useful and make the lives of consumers easier, safer, and less stressful.

Various methods exist for detection of most toxins and harmful substances that might be present in foods or other media. Examples of such methods entail testing in a sealable container (see, e.g., U.S. Pat. No. 6,616,893), with a self-contained swab (see, e.g., U.S. Pat. No. 7,098,040), and a container with multiple ports (see, e.g., U.S. Pat. No. 6,180,335). However, most of the tests that are known in the art are, at the same time, time-consuming and often unrealistic for consumer use because they are bulky and require multiple steps. Such tests are suitable for a laboratory or food manufacturing setting, but not for household use.

Testing methods for substances of interest in food, such as those in the above paragraph, have been around for decades in the form of lateral flow devices (LFD). An example of a LFD is described in U.S. Pat. No. 5,504,013, which is incorporated herein by reference. LFDs can accurately detect substances of interest dissolved in a liquid and are available for a variety of substances. Application of a LFD to detect a substance of interest requires the substance to be dissolved in a liquid. Extracting the substance from food takes time and effort. The food or other test material must be ground up in some form, placed in an appropriate solvent for the substance, and enough time must pass so that the substance is extracted by the solvent. Then, the solvent must be placed in contact with the LFD so the LFD can check the liquid for the substance of interest.

An LFD cannot be placed in the presence of the solvent before the extraction has occurred because, due to the operation of the LFD, it will be rendered useless.

The aforesaid steps and requirements make testing items such as food or cosmetics difficult unless the individual has space, time and knowledge. Providing a platform to accomplish all steps at once in an easy-to-use, portable and fast device would be of great help to millions of individuals.

Devices to aid in the maceration (otherwise referred to herein as "blending") of solid samples, such as food, have been described in the past, however each prior art device has limitations. Examples of prior art maceration devices for consumer food testing may be found in U.S. Pat. Nos. 7,527,765, 7,776,266, and 8,211,715, all to Royds. Royds describes a device that can liquefy food using a reusable blending apparatus, which is not optimal for multiple repeated use in that it requires thorough cleaning between successive uses. Moreover, the Royds device requires multiple user steps to successively mix a sample in a solvent and then to detect toxins. The device taught by Royds does not allow for the liquidized food to be moved from the mixing area to a testing area, therefore the user must administer the test to the food himself or remove the liquefied food and move it to the testing area. In either case, the user's options are compromised, and the test is necessarily less discreet and more cumbersome than might be desired.

The concept of integrating maceration and testing facilities has long been known, and appears, for example, in U.S. Pat. No. 4,822,174, to Deibel. The blending device taught by Deibel is contained within a vessel that allows for continuous mixing inside the vessel with a power supply outside the vessel. In the Deibel device, a rotating mixing blade is driven by a horizontal shaft that couples the blades to the motor. While such devices may be suitable for larger scale mixing, a far simpler one-time-use mixing device would be desirable for the consumer needs outlined above.

SUMMARY OF THE EMBODIMENTS

In accordance with various embodiments of the present invention, a method is provided for testing a medium for the presence of a target analyte. The method has steps of:
a. placing the medium in a capsule, the capsule characterized by a volume, wherein the capsule is provisioned with a solvent and a sensor configured to test for the target analyte;
b. causing the solvent to come into contact with the medium in the capsule;
c. agitating the capsule, thereby agitating the solvent and the medium and creating a dispersion in the solvent of a portion of any target analyte present in the medium;
d. operating a release mechanism configured to cause conduction of the dispersion to the sensor; and
e. producing an indication of presence of the target analyte if the target analyte is present in the medium.

In accordance with other embodiments of the invention, at least a portion of the sensor is visible outside of the capsule. The release mechanism may be a valve disposed in a fluid path between the capsule and a portion of the sensor disposed outside of the capsule. The sensor may be disposed at least partially inside the capsule volume.

In further embodiments of the invention, agitation may be provided by a mixing apparatus. The solvent may be provided in a separate chamber within the capsule; and a valve may be activated to release the solvent to come in contact with the medium. The valve may be actuated by at least one of a mechanical actuator and an electromechanical actuator, and, at least in part, by a force applied by a user. The solvent may be filtered en route to the sensor.

In yet further embodiments, the step of agitating may include operating the mixing apparatus from outside the capsule. Power may be provided to the mixing apparatus by an electromechanical actuator or by a user of the device. The method may include a further step of providing for reading of the sensor by connection through physical, electronic, or electromagnetic methods to an outside housing. The method may also include a further step of transmitting a test result electronically, electromagnetically, or visually to an external device.

In embodiments of the claimed method, the medium may be a consumable or a substance that will come in contact with human or animal skin, and the target analyte may be a food allergen. The target analyte may be chosen from the group of materials causing negative responses in certain humans, including caffeine, phenylalanine, aspartame, MSG, heavy metals, artificial flavors, and artificial colors. Alternatively, the target analyte may be chosen from the group of pathogens including bacteria, viruses, fungus, yeast, pesticides, and other toxins, or from the group of dietary units including fat, protein, sugar, sodium, cholesterol, vitamins, and minerals.

In accordance with another aspect of the present invention, a self-contained portable analysis device is provided. The self-contained portable analysis device has a housing with a capsule insertion port disposed in the housing for releasably receiving a capsule configured to retain a medium. The analysis device also has a sensor holder for retaining a sensor (which may be referred to herein as the "analysis device sensor," to distinguish it from other sensors to which reference is made) and configured to bring the analysis device sensor into contact with contents of the capsule. The analysis device also has a release mechanism, disposed within the housing and coupled to a valve within the capsule; the valve for gating contact between the contents of the capsule and the sensor within the capsule, and the release mechanism configured to cause contact between the contents of the capsule and the sensor. The analysis device sensor can then read the result of the sensor in the capsule, and transmit the result to the user.

In alternate embodiments of the invention, the self-contained portable analysis device may also have a filter disposed in a path traversed by the contents of the capsule antecedent to contact with the sensor. The sensor holder may be integral with the capsule. The self-contained portable analysis device may also have an electromechanical actuator, coupled to the housing, configured to cause mixing of the medium sample and the solvent within the capsule. Furthermore, it may have a transparent or partially opaque viewport allowing the result from the sensor to be read from outside the housing.

In accordance with yet another aspect of the present invention, a capsule is provided for use in a self-contained portable analysis device. The capsule has an enclosed volume for retaining a solvent and a medium sample, a cap adapted to permit introduction of the medium sample into the enclosed volume by a user, and a sensor holder for retaining a sensor and adapted for bringing the sensor in contact with contents of the capsule.

In other embodiments of the invention, the capsule may also have a valve adapted to gate contact between contents of the enclosed volume and the sensor. This valve may be a time driven mechanism such as a dissolvable wall, a timed valve that breaks a seal, or a material that absorbs solution at a known rate. The capsule may have a filter disposed between the contents of the enclosed volume and the sensor. The capsule may also have a metering element built into the cap or capsule, the metering element adapted to permit a specific volume or weight of medium sample into the enclosed capsule volume. The capsule may have a separate chamber adapted for introduction of the solvent and for withdrawal of the solvent upon actuation of a valve. The capsule also may be equipped with a mixer, which, as defined herein, includes mixing blades, grinders, ball bearings or the like, that aid in the mixing of the solvent and the medium to be tested.

BRIEF DESCRIPTION OF THE DRAWINGS

The foregoing features of embodiments will be more readily understood by reference to the following detailed description, taken with reference to the accompanying drawings, in which:

FIG. 1A is a top view of a portable analysis device in accordance with an embodiment of the present invention, while

DETAILED DESCRIPTION OF SPECIFIC EMBODIMENTS

Definitions

As used in this description and the accompanying claims, the following terms shall have the meanings indicated, unless the context otherwise requires:

A "food substrate" is a food substance or an item that comes into contact with a food substance such as a utensil, swab, textile (for example: a napkin or paper) or other similar items. A food substrate is one instance of a "medium" that may be analyzed in accordance with embodiments of the present invention.

A "medium" is any substrate or sample that is to be tested for any of the target analytes. Examples of media, as the term is used herein, include a food substrate, a cosmetic, a lotion or anything that comes into contact with the body of a human or animal. It may also be a consumable, as the term is defined below. Some, but not all, media come in contact with human or animal skin. Examples of media that come in contact with human or animal skin include lotions, creams, soaps, cosmetics, and the like.

A "capsule" is any vial, container or other such item that can hold a liquid, gaseous, or solid material. A "capsule" may be disposable or reusable and may be removable from a larger testing housing or may be permanently affixed.

To "provision" a capsule means to equip with any object or resource needed to facilitate and complete testing for an analyte. This can include but is not limited to chemicals, electrical or mechanical equipment, and sensing devices. Provisioning may occur before, during, or after a test is run.

A "test strip" is any substrate or liquid medium or sensor that provides a detectable response to an analyte for which the device is testing. The "test strip" may take the form of an "actual strip," which is to say a material that is long, narrow and flat, but also includes any other embodiment indicated by the design of the capsule.

An "indication" of presence of the target analyte is any detectable response of the analyte to a sensing medium. This could be in the form of a color change, fluorescence emission, infrared emission, magnetic response, electrical response, acoustic change or other type of detectable response.

A "dispersion" refers to any mixture combining the solvent used for extracting the analyte with a sample of the sampled medium. A "dispersion" may include inhomogeneous mixtures, completely dissolved homogenous mixtures and any variation of the two. Unless expressly distinguished in a particular context, the words dispersion, mixture, solvate and solution are used interchangeably in the present description.

A "valve" is any device for controlling or gating the passage of a liquid, solid, or gas.

Bringing a solvent into contact with a medium resulting in a mixture or solution may be referred to herein as "mixing."

A "sensor" is any substrate or device that can be used to detect the presence of a medium. A "test strip" is an example of one instance of a "sensor."

A "mixer," as the term is used herein, is any structure, such as mixing blades, grinders or the like, that may aid in the mixing of a medium and a solvent.

Interpreting the result from a sensor or test strip, whether visually, electronically, or mechanically, or by other means, may be referred to herein as "reading."

A "consumable," as the term is used herein, includes a solid or a liquid that is consumed by humans or animals, such as a foods, beverages, medicines, and the like.

Figure 1A:
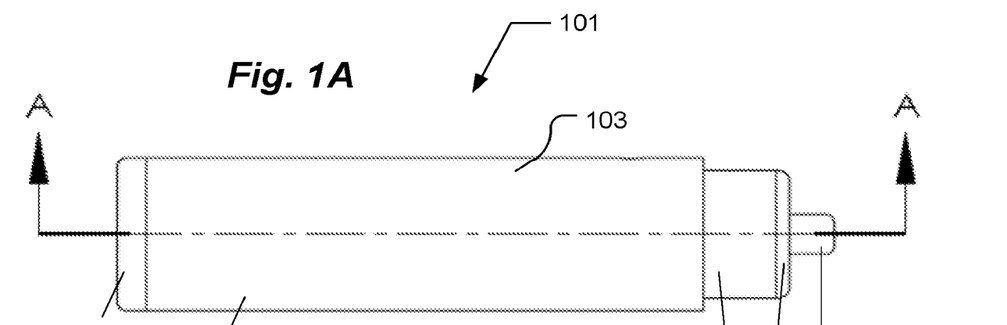
Figure 1B:
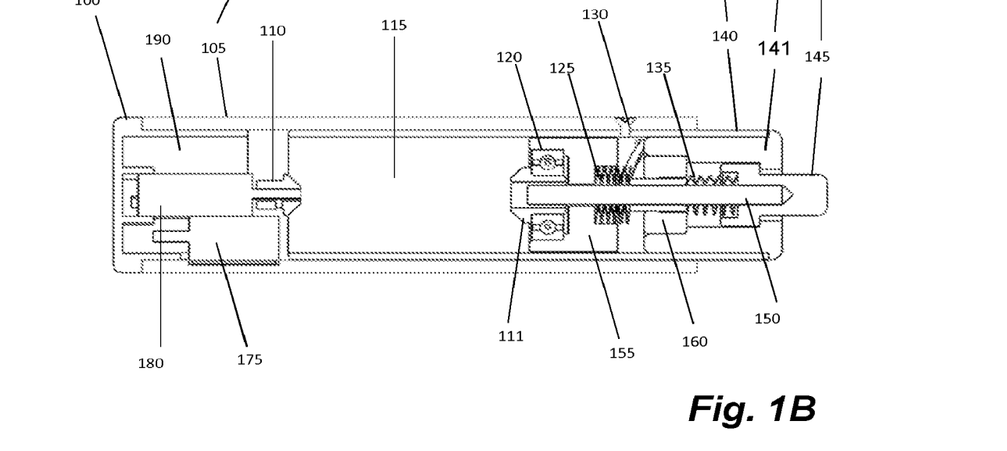
FIG. 1B is a cross-sectional view of salient components of the portable analysis device of FIG. 1A.

Representative embodiments of the present invention are now described with reference to FIGS. 1A and 1B, showing outside and cross sectional views of a self-contained reader/container assembly, designated generally by numeral 101. Reader/container assembly 101 may also be referred to herein as a "reader." The scope of the present invention does not limit the shape or design of the container depicted here, and may be cylindrical, pyramidal, a hybrid of multiple 3D shapes or other shape that may contain a solid or liquid medium for mixing. The housing of the container may be made of plastic, metal or any other material, depending upon design or manufacturing preference and the needs of the user. Contained within the container are all the electrical and mechanical components required to mix the media with the solvent, release the mixture from its containment allowing it to be delivered to the test strip, and read the results of the test strip.

A housing 103 of the reader 101 is composed of a housing left end cap 100, an outer sheath 105, an inner sheath 140, housing right end cap 141, and a compression button 145. These components of the housing 103 enclose electronics (circuit board(s), battery(ies), etc.) 190 for the reader, a motor to drive the mixing 180, a solenoid 175 to properly align a disposable capsule 200 (shown in FIG. 4A) so that test strip 299 (shown in FIG. 4B) may be positioned correctly in test strip holder 235 to be read by the reader, a housing slot for the capsule 115, and the associated equipment to release the media/solvent mixture inside the capsule 200 to the test strip 299, as now described.

A mechanism for releasing the fluid inside the capsule may include a button 145 connected to a valve release rod 150 that opens a valve in the capsule when actuated. The valve release rod 150 is aligned by a bushing 160, and is returned back into starting position by a compression spring 135.

Once inserted into the reader 101, the capsule is aligned axially by mating the bearing/capsule female coupling 261 (shown in FIG. 4B) with the bearing/capsule male coupling 111. The bearing/capsule male coupling 111 is fitted into a bearing 120 which is fitted into the sliding compression mount 155. When the reader is closed, compression spring 125 forces the capsule to contact the motor/capsule coupling 110 on one end, and the bearing/capsule coupling 111 on the other end. This aligns and constrains the capsule axially, and allows it to rotate with the motor 180 and bearing 120. In an alternate embodiment of the invention, this agitation mechanism, or another agitation mechanism involving internal blades, a grinder, a grater, vibration, etc., may be operated through a drive-shaft, gearing, electromechanical, magnetic, or other means.

Figure 2A:
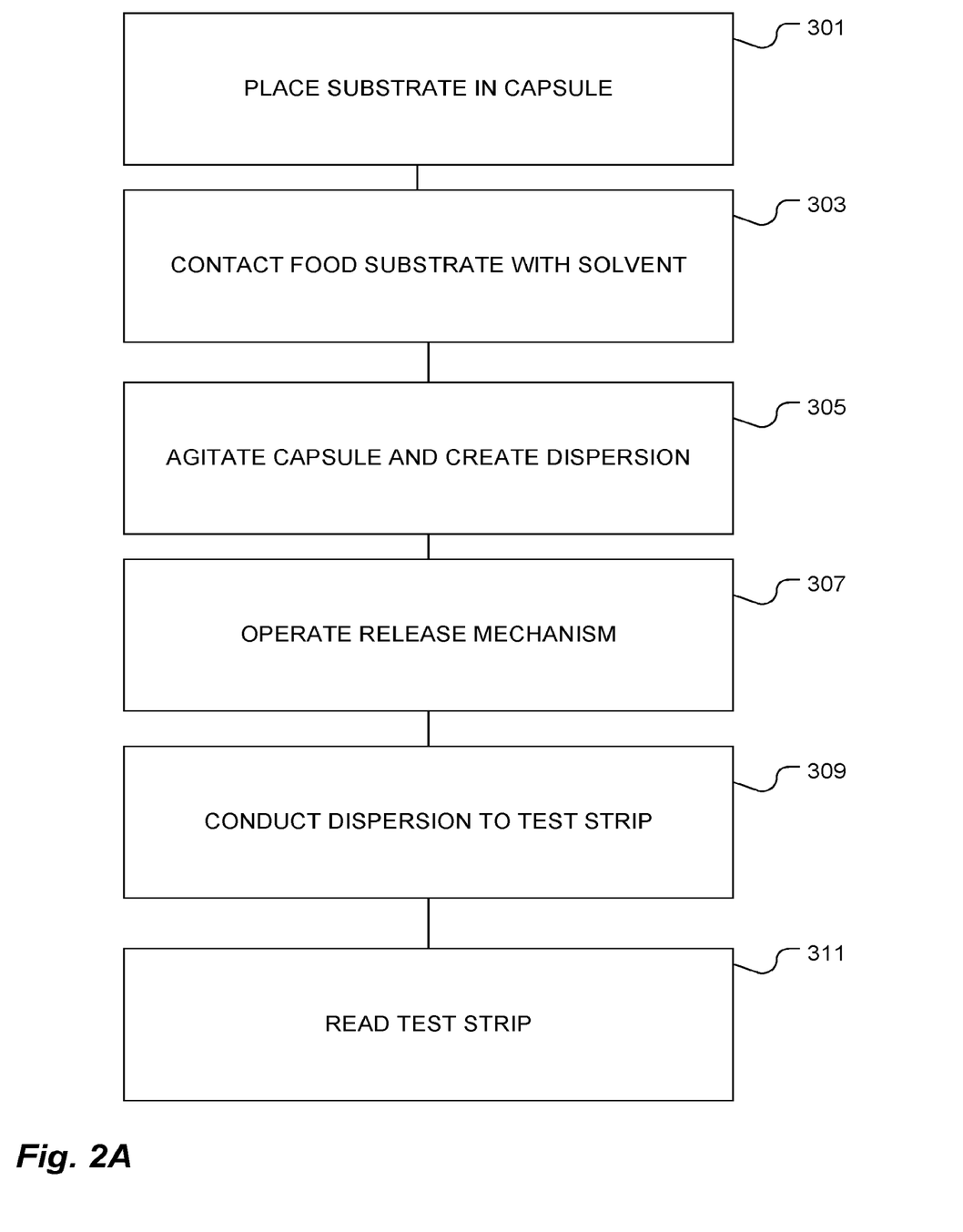
FIGS. 2A and 2B are flowcharts depicting processes for consumer analysis of samples for detection of harmful constituents, in accordance with certain embodiments of the present invention.

The flowchart of FIG. 2A depicts steps in the processing of a food sample, or substrate, in accordance with certain embodiments of the present invention. In a first step 301, a medium 260 (shown in FIG. 4B) is placed into capsule 200, wherein the capsule is provisioned with a solvent and a test strip configured to test for the target analyte. The solvent is caused, in step 303, to come into contact with the medium in the capsule. The capsule, powered by a motor directly by the user, is agitated 305 so as to mix the solvent and medium and to enhance dispersing or dissolving, thereby creating a dispersion, in the solvent, of a portion of any target analyte present in the medium. A release mechanism is operated 307 in such a way as to cause conduction 309 of the dispersion to the test strip 299 (shown in FIG. 4B), so that test strip 299 produces an indication of presence of the target analyte if the target analyte is present in the medium. Any such indication may then be read 311, either by a user or automatically (i.e., by an electrical sensor in the device).

Figure 2B:
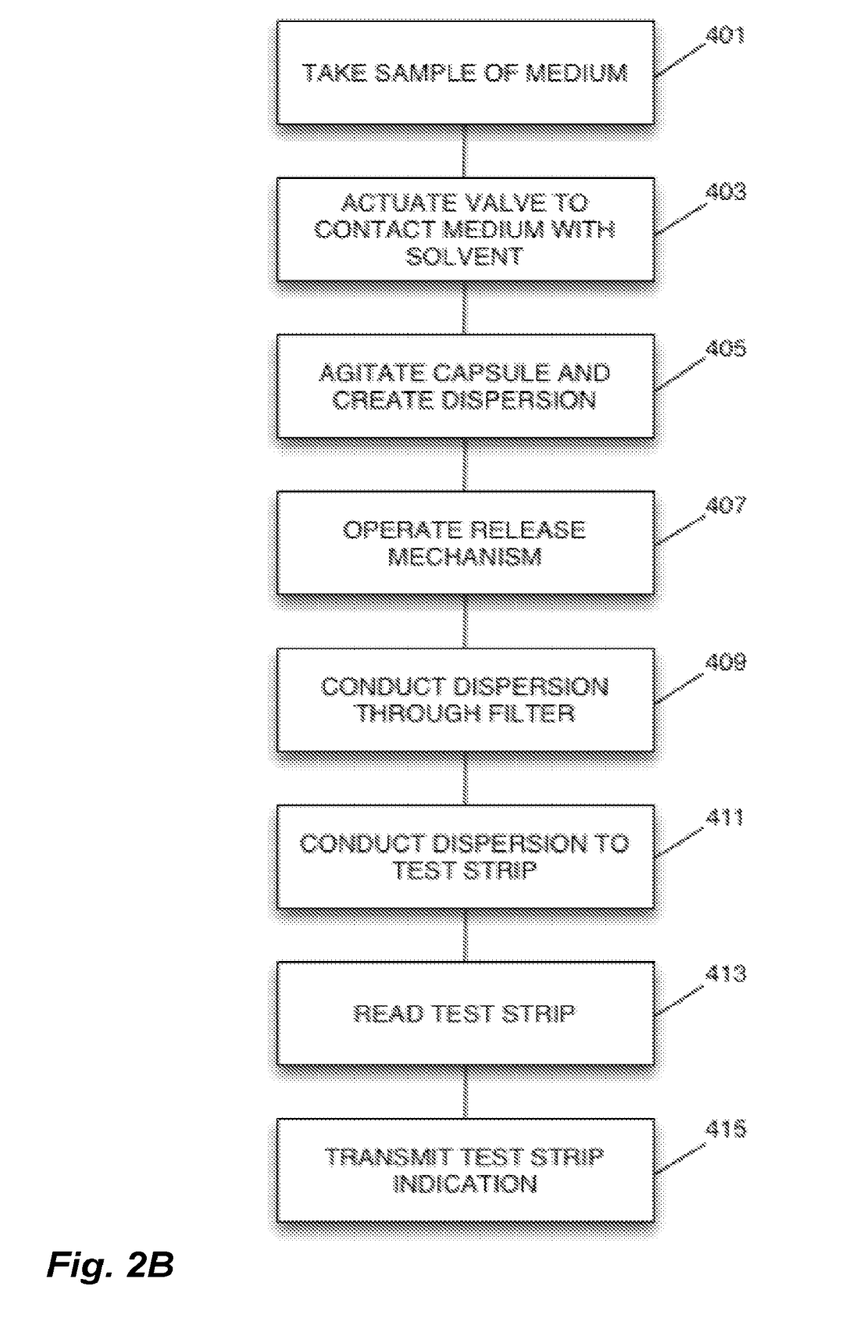

The flowchart in FIG. 2B depicts steps in the processing of medium 260 in accordance with an alternate embodiment of the present invention. In the first step 401, the medium is sampled by an apparatus 210, built into capsule 200, wherein the capsule is provisioned with a solvent and a test strip 299 configured to test for the target analyte. In one embodiment of the invention, apparatus 210 samples a specific and pre-defined volume or weight of the medium being tested. In one embodiment of the invention, the solvent is provisioned within a separate chamber 250 in the capsule 200, until a valve 255 is actuated to release the solvent to come in contact with the medium 260. Valve 255 may be actuated by a mechanical device such as a spring, lever, etc., or by an electromechanical device such as a motor, solenoid, etc., or by force applied from the user. Medium 260 is then agitated (405) within the capsule, with agitation driven by a motor, ultrasonic actuator, the user, etc., in order to create a dispersion of any portion of the target analyte present in the medium. In one embodiment, a release mechanism is operated (407) in such a way as to cause conduction of the dispersion through a filter (409) in order to filter out any solid particles or other material that could affect the validity or sensitivity of the test, thereby improving the detection of the test. The filter is disposed between the solvent and/or medium and the sensor. The dispersion is then conducted (411) to the test strip, so that the test strip produces an indication of presence of the target analyte if the target analyte is present in the medium. Any such indication may then be read (413) either by a user or automatically. This indication may then be transmitted (415) electronically, magnetically, electromagnetically, visually, mechanically, through radio-frequency, etc. to a mobile phone, tablet, computer, or other device, including devices of a 3rd party device.

Figures 3A, 3B:
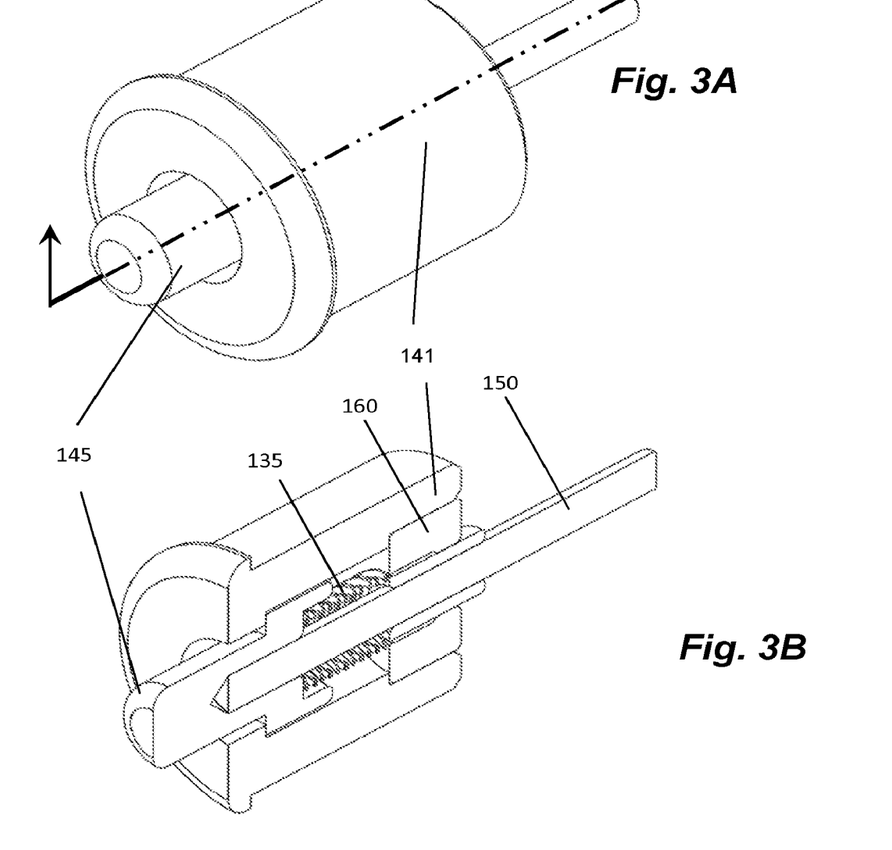
FIGS. 3A and 3B are perspective outside and cross-sectional views, respectively, of a top end cap containing components for releasing a valve in a capsule, in accordance with embodiments of the present invention.

FIGS. 3A and 3B are perspective outer and cross sectional views of the top end cap 141 (shown in FIG. 1B) containing all the components required to release the valve on the capsule. Components of FIGS. 3A and 3B also appear in FIG. 1. In the embodiment of the invention depicted in FIGS. 3A and 3B, the release rod is inserted by the user, but, within the scope of the present invention, insertion may also be by any electro-mechanical means such as a solenoid, for example.

Figures 4A, 4B:
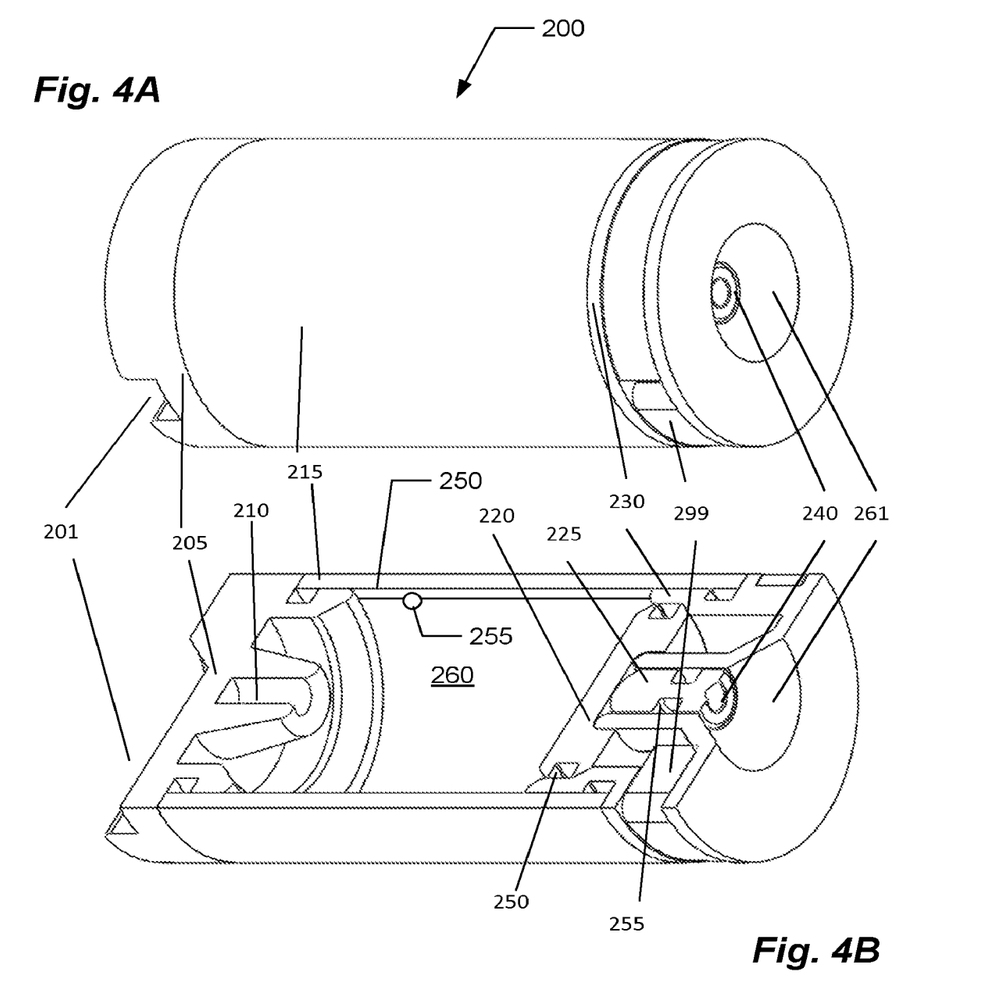
FIGS. 4A and 4B are perspective outside and cross-sectional views, respectively, of a capsule used to mix and test a medium, in accordance with embodiments of the present invention.

Referring now to FIGS. 4A and 4B, outer and cross sectional views are shown of the capsule 200 used to mix and test the media. The capsule is comprised the left capsule end cap 205, right capsule end cap 230, and capsule shell 215. Cut into the left end cap 205 is an alignment slot 201 that allows for the solenoid to engage and properly align the capsule, after mixing, for correct reading of the test strip used. The left end cap 205 also contains a holder for any utensil, such as a swab or spoon, which may be used to gather food and insert into the capsule and a female slot 261 for coupling with the mixing motor. In this embodiment the motor is coupled through a compression fitting, although many types of mechanical, electrical or magnetic coupling would work.

The left end cap 205 is a compression fitted cap that can be removed to allow food or other media to be inserted into the capsule. Once food or other media is put into the capsule the left end cap 205 is replaced onto the capsule housing 215 and the capsule is then inserted into the housing 101 at the position designated by numeral 115 in FIG. 1. The right end cap 230 contains the valve door 220 (otherwise referred to herein as a "valve"), valve release rod coupling 225, and an insertion slot 240 for the release rod. When the reader is closed, the motor/capsule female coupling 261 is compressed into the motor/capsule male coupling port 110 (shown in FIG. 1) so that torque can be transmitted from the motor to the capsule, which is required for mixing to begin. Once mixing is completed the release rod 150 (shown in FIG. 1) is pushed into the insertion slot 240 for the release rod. This opens the valve door 220 by pushing the valve release rod coupling 225 open and allows the mixture inside the capsule to contact a sensor, of which test strip 299 is an example. The test strip 299 is connected to the valve and is sent outside the capsule via the test strip exit slot 245 so it can be read by the reader (FIG. 1). In some embodiments of the invention, at least a portion of the sensor is visible outside the capsule. In other embodiments of the invention, at least a portion of the sensor is disposed outside the capsule.

Figure 5:
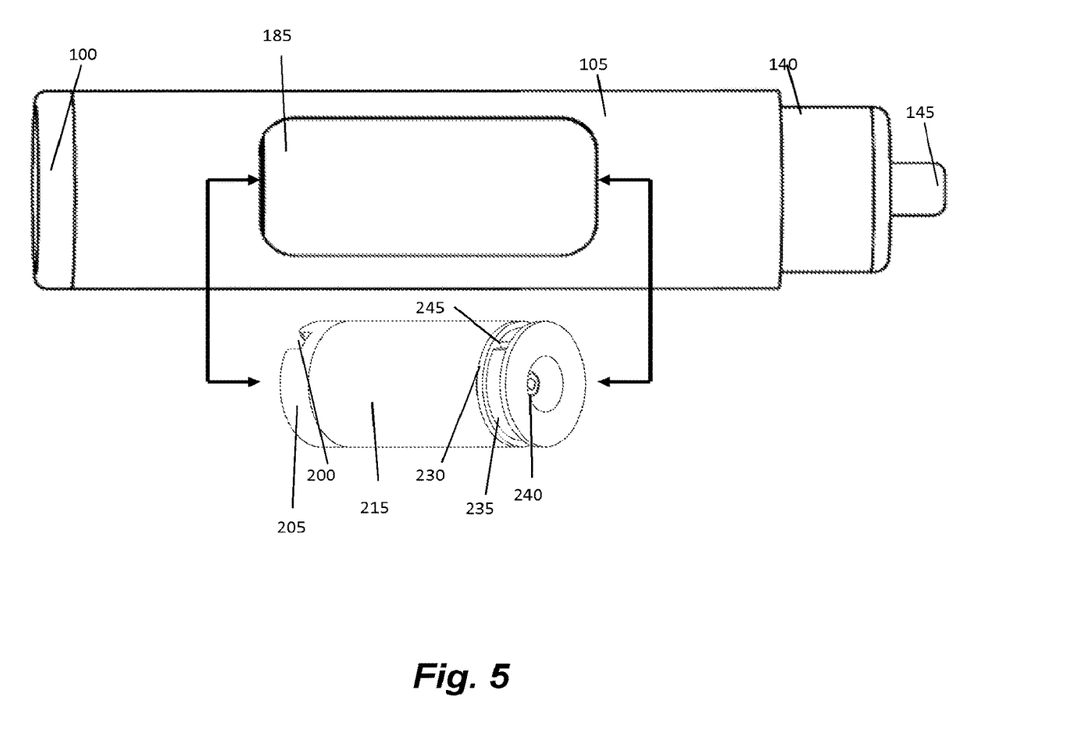
FIG. 5 shows a capsule and a reader and schematically depicts insertion of the capsule into the reader in accordance with embodiments of the present invention.

FIG. 5 shows capsule 200 and reader 101 together and how capsule 200 is inserted into reader 101. The outside sheath 105 of the reader is rotated to open the holding area for the capsule 115. The capsule is placed directly into the capsule insertion port 185 and the sheath 105 is then rotated closed. The compression spring 135 (shown in FIG. 1) compresses the capsule female motor coupling port 261 onto the male motor coupling and locks the capsule in place, at which point testing can begin.

In certain embodiments of the invention, the apparatus described herein is used to extract samples potentially containing toxins or other analytes from specific media and to deliver any extracted toxins to an appropriate sensor. The sampled medium may be any medium that may be consumed or that may contact an individual or animal. Examples include foods, drinks, medicines, vitamins, cosmetics, lotions, etc., all recited without limitation, and may also include any medium that has come into contact with a consumable item. The toxins for which testing is performed may be anything that produces a negative response from the individual or animal such as a poison, a bacterium, a fungus, an allergen, pesticides, MSG, heavy metals, etc. The toxins tested for may also be anything that an individual may want to monitor intake levels of such as caffeine, phenylalanine, aspartame, artificial flavors or colors, fat, proteins, sugars, sodium, cholesterol, vitamins, minerals, etc. The target analyte may also be chosen from the group of pathogens including bacteria, fungus, yeast, pesticides, and other toxins. The target analyte may also be a dietary unit chosen from the group including fat, protein, sugar, sodium, cholesterol, vitamins, and minerals.

The testing device consists of two main components; a container 200 that mixes the sampled medium, with an extraction solution and delivers the extraction solution to a sensor, and a housing unit that powers the mixer and reads the result of the sensor. Depending on the specific embodiment of the sensor, such as a visually-based sensor, the housing unit may or may need to read the result of the sensor. Test strip 299 is an example of such a sensor.

This device described in accordance with the present invention may advantageously allow individuals to rapidly test any consumer product that may contain a substance harmful to them. For example, many foods contain allergens that cause a multitude of problems from rashes and gastric distress to anaphylactic shock. Consumers who are affected by one of these allergens currently have no rapid method to test any food they encounter so they must be extremely sure of the content of the food or avoid it completely. Devices in accordance with the present invention, however, allow the consumer to test a small sample of the food very quickly to determine if it contains any harmful contaminants to them.

It should be understood that, within the scope of the present invention, the medium to be sampled may be placed into capsule 200 that contains a solvent designed to extract a specific analyte contained within the media. The sampled medium may be placed into the capsule directly or may be added via a tool such as a swab, spoon or other utensil. Capsule 200 is equipped with a sensor (of which test strip 299 is an example) that will detect the presence of the target analyte. The sensor may be in the form of a strip, such as a lateral flow device, or another type of sensor, now known or later invented, that displays results in a variety of forms such as color change, spectral emission, magnetic, electrical current or bias, acoustic or any other known sensing method.

Once the food substrate or other sampled medium is placed into capsule 200, the capsule is placed into a reader housing 103 where the sampled medium and the solvent are mixed together to enhance extraction of the target analyte. In the embodiment described herein the mixing is caused by rotating or oscillating capsule 200 to create agitation, but it is to be understood that any other embodiment of mixing, using apparatus such as blades, grinders, shakers, or agitators, provided by way of example, are within the scope of the present invention. Power may be supplied to the mixing by means of a motor rotating the capsule, a motor rotating the mixing agitators, ultrasonic actuation, or magnetically, all recited by way of example. Mixing enhancers such as ball bearings or the like, contained within the capsule, may be employed in conjunction with any of the aforesaid mixing modalities. All of the forgoing are non-exhaustive examples of mixing apparatus. The mixing apparatus may be adapted for operation from outside the capsule, as through a driveshaft, gearing, electro-mechanical, magnetic or other means. Power may be supplied to the mixing device by the user, as by manually turning the grinders, pushing the medium through a grinding, grating or mixing apparatus, manually shaking, or rotating the device, all recited by way of example.

After mixing is complete, capsule 200 releases the solvent/media mixture so the solution contacts the test being used. In one embodiment of the invention, a valve 220 is used to release the mixture to the sensor, and, more particularly, to a portion of the sensor that is disposed outside of the capsule. However any number of mixture release mechanisms could be used. Valve 220 may be actuated by a mechanical actuator or an electromagnetic actuator, or both. A spring and a lever are non-exhaustive examples of mechanical actuators. A motor, a solenoid and an electromagnet are non-exhaustive examples of electromechanical actuators.

Once the mixture reaches the sensor, the sensor checks the mixture for the presence of the target analyte, and the reader determines the result of the test. If the test is positive, an indication, either through indicator lights, a visual screen, or other mechanical or optical means, displays the positive result, or similarly displays a negative result for the target analyte. A test result may be transmitted to an external device. The external device may be a third-party device, and it may be a mobile phone, tablet, or computer, for example.

Embodiments of the invention described above are intended to be merely exemplary; numerous variations and modifications will be apparent to those skilled in the art. All such variations and modifications are intended to be within the scope of the present invention as defined in any appended claims.

What is claimed is:

1. A capsule for use in a self-contained portable analysis device, the capsule comprising:
   an enclosed volume for retaining a solvent and a medium sample;
   a cap adapted to permit introduction of the medium sample into the enclosed volume by a user;
   a sensor holder for retaining a sensor and adapted for bringing the sensor in contact with contents that include at least a portion of the medium sample mixed with the solvent in the enclosed volume;
   a female coupling at an end of the capsule;
   wherein the capsule is configured to be received within the self-contained portable analysis device;
   wherein a male coupling port of the self-contained portable analysis device is configured to be received within the female coupling of the capsule; and
   wherein when the capsule is positioned within the self-contained portable analysis device and the male coupling port of the self-contained portable analysis device is positioned within the female coupling of the capsule a motor of the self-contained portable analysis device is configured to transmit torque to the capsule to rotate the capsule.

2. The capsule in accordance with claim 1, further comprising a valve positioned between the enclosed volume and the sensor, the valve being adapted to be opened to allow the contents to move into contact the sensor; and
   wherein the valve is actuated by a mechanical device including a spring;
   wherein the valve is configured to break a seal to allow the contents to contact the sensor.

3. The capsule in accordance with claim 1, further comprising a filter disposed between the enclosed volume and the sensor.

4. The capsule in accordance with claim 1, further comprising the sensor that is a test strip that is configured to test for a target analyte that is a food allergen.

5. The capsule in accordance with claim 1, wherein a motor of the self-contained portable analysis device is configured to be magnetically coupled to the capsule.

6. The capsule in accordance with claim 1, wherein the capsule comprises a grinder configured to process the medium sample within the capsule; and
   wherein a motor of the self-contained portable analysis device is configured to rotate the capsule.

7. The capsule in accordance with claim 1, wherein the capsule is configured to be axially aligned with the self-contained portable analysis device.

8. The capsule in accordance with claim 1, wherein the capsule includes a valve adapted to be opened to allow the contents to move out of the enclosed volume and then to contact the sensor; and
   wherein the self-contained portable analysis device is configured to open the valve.

9. The capsule in accordance with claim 1, wherein the sensor includes a test strip that is configured to produce an indication of a presence of a target analyte, based on the target analyte being present in the medium sample.

10. The capsule in accordance with claim 1, wherein the medium sample is a food substrate.

11. The capsule in accordance with claim 1, wherein the capsule is configured to be agitated to mix the medium sample and the solvent together in the enclosed volume.

12. The capsule in accordance with claim 11, wherein the capsule is configured to be agitated by force applied from the user.

13. The capsule in accordance with claim 1, wherein the cap includes a holder configured to be coupled to a utensil.

14. The capsule in accordance with claim 13, wherein the utensil is a spoon.

15. The capsule in accordance with claim 1, further comprising a housing that defines the enclosed volume; and
   wherein the cap is removably coupled to the housing.

16. A capsule comprising:
   a capsule housing defining an enclosed volume for retaining a solvent and a medium sample;
   a cap adapted to permit introduction of the medium sample into the enclosed volume by a user;
   a sensor including a test strip that is configured to test for a target analyte that is a food allergen;
   a sensor holder that is configured to retain the sensor and adapted for bringing the sensor in contact with contents that include at least a portion of the medium sample mixed with the solvent in the enclosed volume;
   a valve configured to open to allow the contents to leave the enclosed volume and then to contact the sensor;
   wherein the capsule is configured to be received within a self-contained portable analysis device; and
   wherein a motor of the self-contained portable analysis device is configured to be magnetically coupled to the capsule.

17. The capsule of claim 16, wherein the enclosed volume is isolated from the ambient environment.

18. A capsule comprising:
a capsule housing defining an enclosed volume for retaining a solvent and a medium sample;
a cap adapted to permit introduction of the medium sample into the enclosed volume by a user;
a sensor including a test strip that is configured to test for a target analyte that is a food allergen;
a sensor holder that is configured to retain the sensor and adapted for bringing the sensor in contact with contents that include at least a portion of the medium sample mixed with the solvent in the enclosed volume;
a valve configured to open to allow the contents to leave the enclosed volume and then to contact the sensor;
a female coupling at an end of the capsule;
wherein the capsule is configured to be received within a self-contained portable analysis device;
wherein a male coupling port of the self-contained portable analysis device is configured to be received within the female coupling of the capsule; and
wherein when the capsule is positioned within the self-contained portable analysis device and the male coupling port of the self-contained portable analysis device is positioned within the female coupling of the capsule a motor of the self-contained portable analysis device is configured to transmit torque to the capsule to rotate the capsule.

19. The capsule of claim 16, wherein the valve is configured to break a seal to allow the contents to contact the sensor.

* * * * *